United States Patent
Kang et al.

(10) Patent No.: US 11,707,426 B2
(45) Date of Patent: *Jul. 25, 2023

(54) COLOR PROTECTANT COMPOSITIONS

(71) Applicant: Living Proof, Inc., Boston, MA (US)

(72) Inventors: Soo-Young Kang, Bedford, MA (US); Zhaoxia Ji, Natick, MA (US); Sara A. Turner, Boston, MA (US); Ling-Fang Tseng, Boston, MA (US); Dinara A. Villanueva, Boston, MA (US); Eric G. Spengler, Boston, MA (US)

(73) Assignee: Living Proof, Inc., Boston, MA (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/326,605

(22) Filed: May 21, 2021

(65) Prior Publication Data

US 2022/0105021 A1 Apr. 7, 2022

Related U.S. Application Data

(63) Continuation of application No. 17/071,198, filed on Oct. 15, 2020, now abandoned, which is a continuation of application No. 16/128,622, filed on Sep. 12, 2018, now Pat. No. 10,842,729.

(60) Provisional application No. 62/655,275, filed on Apr. 10, 2018, provisional application No. 62/557,825, filed on Sep. 13, 2017.

(51) Int. Cl.
| | |
|---|---|
| *A61K 8/87* | (2006.01) |
| *A61Q 5/00* | (2006.01) |
| *A61K 8/36* | (2006.01) |
| *A61K 8/365* | (2006.01) |
| *C08G 18/66* | (2006.01) |
| *C08G 18/32* | (2006.01) |
| *C08G 18/44* | (2006.01) |
| *A61K 8/02* | (2006.01) |
| *C08G 18/08* | (2006.01) |
| *C08G 18/75* | (2006.01) |
| *C08G 18/34* | (2006.01) |

(52) U.S. Cl.
CPC .............. *A61K 8/87* (2013.01); *A61K 8/0241* (2013.01); *A61K 8/361* (2013.01); *A61K 8/365* (2013.01); *A61Q 5/004* (2013.01); *C08G 18/0809* (2013.01); *C08G 18/0833* (2013.01); *C08G 18/3206* (2013.01); *C08G 18/3275* (2013.01); *C08G 18/348* (2013.01); *C08G 18/44* (2013.01); *C08G 18/6655* (2013.01); *C08G 18/6659* (2013.01); *C08G 18/755* (2013.01); *A61K 2800/413* (2013.01); *A61K 2800/5426* (2013.01); *A61K 2800/654* (2013.01); *A61K 2800/884* (2013.01)

(58) Field of Classification Search
None
See application file for complete search history.

(56) References Cited

U.S. PATENT DOCUMENTS

| | | |
|---|---|---|
| 3,104,424 A | 9/1963 | Immel |
| 3,262,686 A | 7/1966 | Kraus et al. |
| 3,803,063 A | 4/1974 | Krentz, Jr. |
| 3,973,901 A | 8/1976 | Micchelli et al. |
| 4,071,614 A | 1/1978 | Grimm, III |
| 4,455,146 A | 6/1984 | Noda et al. |
| 4,950,542 A | 8/1990 | Barker |
| 5,110,852 A | 5/1992 | Gogolewski et al. |
| 5,281,654 A | 1/1994 | Eisenhart et al. |
| 5,290,543 A | 3/1994 | Ounanian et al. |
| 5,335,373 A | 8/1994 | Dresdner, Jr. et al. |
| 5,357,636 A | 10/1994 | Dresdner, Jr. et al. |
| 5,362,486 A | 11/1994 | Nandagiri et al. |
| 5,534,265 A | 7/1996 | Fowler et al. |
| 5,534,348 A | 7/1996 | Miller et al. |
| 5,540,853 A | 7/1996 | Trinh et al. |
| 5,626,840 A | 5/1997 | Thomaides et al. |
| 5,637,291 A | 6/1997 | Bara et al. |
| 5,643,581 A | 7/1997 | Mougin et al. |
| 5,720,961 A | 2/1998 | Fowler et al. |
| 5,733,572 A | 3/1998 | Unger et al. |
| 5,807,540 A | 9/1998 | Junino et al. |
| 5,833,967 A | 11/1998 | Ramin |
| 5,846,551 A | 12/1998 | DaCunha et al. |
| 5,849,310 A | 12/1998 | Trinh et al. |
| 5,891,463 A | 4/1999 | Dello et al. |
| 5,900,457 A | 5/1999 | Duan et al. |
| 5,912,299 A | 6/1999 | Tomko et al. |
| 5,914,117 A | 6/1999 | Lavaud |
| 5,932,194 A | 8/1999 | Plessix et al. |
| 5,932,200 A | 8/1999 | Reich et al. |
| 5,993,972 A | 11/1999 | Reich et al. |

(Continued)

FOREIGN PATENT DOCUMENTS

| | | |
|---|---|---|
| BR | PI0405064 A | 8/2005 |
| BR | 102013022835 A2 | 8/2015 |

(Continued)

OTHER PUBLICATIONS

Ma et al., Synthetic Leather Chemistry and Technology, 1st Edition. 4 pages, Nov. 30, 2015.
Chinese Office Action for Application No. 201980028764.2, dated Dec. 6, 2022, 17 pages.
U.S. Appl. No. 15/451,897, filed Mar. 7, 2017, 2017-0258700, Allowed.
U.S. Appl. No. 16/348,644, filed May 9, 2019, 2019-0359786, Abandoned.
U.S. Appl. No. 16/128,620, filed Sep. 12, 2018, U.S. Pat. No. 10,987,300, Issued.
U.S. Appl. No. 17/231,587, filed Apr. 15, 2021, Abandoned.
U.S. Appl. No. 17/530,662, filed Nov. 19, 2021, Abandoned.

(Continued)

*Primary Examiner* — Brian Gulledge
(74) *Attorney, Agent, or Firm* — McCarter & English, LLP; Michael J. DeGrazia

(57) ABSTRACT

Provided herein are color protectant compositions for dyed human hair, and methods for determining the same.

17 Claims, 4 Drawing Sheets

(56) References Cited

U.S. PATENT DOCUMENTS

| | | |
|---|---|---|
| 6,007,793 A | 12/1999 | Bhatt et al. |
| 6,084,051 A | 7/2000 | Blum et al. |
| 6,086,903 A | 7/2000 | Trinh et al. |
| 6,106,813 A | 8/2000 | Mondet et al. |
| 6,126,930 A | 10/2000 | Dubois et al. |
| 6,130,309 A | 10/2000 | Reich et al. |
| 6,132,704 A | 10/2000 | Bhatt et al. |
| 6,153,179 A | 11/2000 | Blankenburg et al. |
| 6,156,325 A | 12/2000 | Farer et al. |
| 6,221,344 B1 | 4/2001 | Ramin et al. |
| 6,238,651 B1 | 5/2001 | Bara |
| 6,254,876 B1 | 7/2001 | de la Poterie et al. |
| 6,277,386 B1 | 8/2001 | Kim et al. |
| 6,277,401 B1 | 8/2001 | Bello et al. |
| 6,291,580 B1 | 9/2001 | Kukkala et al. |
| 6,298,558 B1 | 10/2001 | Tseng et al. |
| 6,319,959 B1 | 11/2001 | Mougin et al. |
| 6,326,013 B1 | 12/2001 | Lemann et al. |
| 6,346,234 B1 | 2/2002 | Rollat et al. |
| 6,361,782 B1 | 3/2002 | Chevalier et al. |
| 6,365,697 B1 | 4/2002 | Kim et al. |
| 6,372,876 B1 | 4/2002 | Kim et al. |
| 6,403,070 B1 | 6/2002 | Pataut et al. |
| 6,403,107 B1 | 6/2002 | Lemann |
| 6,403,542 B1 | 6/2002 | Maurin et al. |
| 6,409,998 B1 | 6/2002 | Candau et al. |
| 6,433,073 B1 | 8/2002 | Kantner et al. |
| 6,465,534 B2 | 10/2002 | Fukuzawa et al. |
| 6,469,227 B1 | 10/2002 | Cooke et al. |
| 6,485,950 B1 | 11/2002 | Kumar et al. |
| 6,517,821 B1 | 2/2003 | Rollat et al. |
| 6,520,186 B2 | 2/2003 | Rollat et al. |
| 6,524,564 B1 | 2/2003 | Kim et al. |
| 6,524,597 B2 | 2/2003 | Kashimoto |
| 6,531,118 B1 | 3/2003 | Gonzalez et al. |
| 6,555,096 B2 | 4/2003 | Carrion et al. |
| 6,576,024 B1 | 6/2003 | Lang et al. |
| 6,576,702 B2 | 6/2003 | Anderle et al. |
| 6,579,517 B1 | 6/2003 | Kim et al. |
| 6,592,881 B1 | 7/2003 | Fukuda et al. |
| 6,613,314 B1 | 9/2003 | Rollat et al. |
| 6,635,262 B2 | 10/2003 | Jourdan et al. |
| 6,641,804 B1 | 11/2003 | Ohta et al. |
| 6,682,748 B1 | 1/2004 | De La Poterie et al. |
| 6,689,345 B2 | 2/2004 | Jager Lezer |
| 6,692,729 B1 | 2/2004 | Asaoka et al. |
| 6,719,959 B1 | 4/2004 | Gonzalez et al. |
| 6,730,289 B2 | 5/2004 | Khoshdel |
| 6,750,291 B2 | 6/2004 | Kim et al. |
| 6,800,276 B2 | 10/2004 | Kim et al. |
| 6,830,758 B2 | 12/2004 | Nichols et al. |
| 6,884,853 B1 | 4/2005 | Asaoka et al. |
| 6,897,281 B2 | 5/2005 | Lubnin et al. |
| 6,927,254 B2 | 8/2005 | Melchiors et al. |
| 7,019,061 B2 | 3/2006 | Meffert et al. |
| 7,098,178 B2 | 8/2006 | Gerke et al. |
| 7,101,954 B2 | 9/2006 | Zofchak et al. |
| 7,160,553 B2 | 1/2007 | Gibbins et al. |
| 7,326,256 B2 | 2/2008 | Cottard et al. |
| 7,348,299 B2 | 3/2008 | Keenan et al. |
| 7,445,770 B2 | 11/2008 | Berezkin et al. |
| 7,452,525 B1 | 11/2008 | Berezkin et al. |
| 7,481,996 B2 | 1/2009 | Ishii et al. |
| 7,659,233 B2 | 2/2010 | Hurley et al. |
| 7,700,082 B2 | 4/2010 | Mallo et al. |
| 7,740,832 B1 | 6/2010 | Rollat-Corvol et al. |
| 7,744,911 B2 | 6/2010 | Pechko et al. |
| RE41,615 E | 8/2010 | Kim et al. |
| 7,829,099 B2 | 11/2010 | Woeller et al. |
| 7,907,346 B2 | 3/2011 | Swarup et al. |
| 7,914,775 B2 | 3/2011 | Cottard et al. |
| 7,959,903 B2 | 6/2011 | Candau et al. |
| 7,972,589 B2 | 7/2011 | Leighton et al. |
| 7,998,465 B2 | 8/2011 | De La Poterie et al. |
| 8,067,355 B2 | 11/2011 | Smets et al. |
| 8,258,093 B2 | 9/2012 | Van Dyke |
| 8,343,523 B2 | 1/2013 | Toreki et al. |
| 8,449,871 B2 | 5/2013 | Mougin et al. |
| 8,497,338 B2 | 7/2013 | Bai et al. |
| 8,623,388 B2 | 1/2014 | Rajaiah et al. |
| 8,629,213 B2 | 1/2014 | Hidalgo et al. |
| 8,679,050 B2 | 3/2014 | Nakamura |
| 8,679,465 B2 | 3/2014 | Malnou |
| 8,734,772 B1 | 5/2014 | Zhou et al. |
| 8,741,333 B2 | 6/2014 | Zhang et al. |
| 8,784,854 B2 | 7/2014 | Choi et al. |
| 8,871,817 B2 | 10/2014 | Turk et al. |
| 8,882,902 B2 | 11/2014 | Suzuki et al. |
| 8,895,040 B2 | 11/2014 | Vondruska et al. |
| 8,956,160 B2 | 2/2015 | Willison et al. |
| 8,956,162 B2 | 2/2015 | De Vreese et al. |
| 9,016,221 B2 | 4/2015 | Brennan et al. |
| RE45,538 E | 6/2015 | Smets et al. |
| 9,079,152 B2 | 7/2015 | Markus et al. |
| 9,101,143 B2 | 8/2015 | Markus et al. |
| 9,102,783 B2 | 8/2015 | Yagi et al. |
| 9,175,125 B2 | 11/2015 | Turk et al. |
| 9,295,632 B1 | 3/2016 | Benn et al. |
| 9,340,650 B2 | 5/2016 | Wagner et al. |
| 9,393,218 B2 | 7/2016 | Zurdo Schroeder et al. |
| 10,842,729 B2 | 11/2020 | Kang et al. |
| 10,987,300 B2 | 4/2021 | Kang et al. |
| 2001/0031280 A1 | 10/2001 | Ferrari et al. |
| 2002/0028875 A1 | 3/2002 | Anderle et al. |
| 2002/0034480 A1 | 3/2002 | Grimm et al. |
| 2002/0034486 A1 | 3/2002 | Midha et al. |
| 2002/0102222 A1 | 8/2002 | Carrion et al. |
| 2002/0107314 A1 | 8/2002 | Pinzon et al. |
| 2002/0114773 A1 | 8/2002 | Kanji et al. |
| 2002/0155962 A1 | 10/2002 | Cincotta et al. |
| 2002/0164297 A1 | 11/2002 | Ferrari et al. |
| 2002/0192273 A1 | 12/2002 | Buseman et al. |
| 2003/0026815 A1 | 2/2003 | Scott et al. |
| 2003/0064086 A1 | 4/2003 | Carrion et al. |
| 2003/0082126 A9 | 5/2003 | Pinzon et al. |
| 2003/0086886 A1 | 5/2003 | Midha |
| 2003/0086896 A1 | 5/2003 | Midha et al. |
| 2003/0099694 A1 | 5/2003 | Cevc et al. |
| 2003/0125427 A9 | 7/2003 | Pinzon et al. |
| 2003/0185780 A1 | 10/2003 | Ferrari et al. |
| 2003/0190345 A1 | 10/2003 | Cordes et al. |
| 2003/0191154 A1 | 10/2003 | Kalafsky et al. |
| 2003/0198659 A1 | 10/2003 | Hoffmann et al. |
| 2003/0203991 A1 | 10/2003 | Schottman et al. |
| 2004/0001798 A1 | 1/2004 | Perron et al. |
| 2004/0057914 A1 | 3/2004 | Bonda et al. |
| 2004/0071757 A1 | 4/2004 | Rolf |
| 2004/0086482 A1 | 5/2004 | Zofchak et al. |
| 2004/0120915 A1 | 6/2004 | Yang et al. |
| 2004/0131573 A1 | 7/2004 | Tang |
| 2004/0137028 A1 | 7/2004 | de la Poterie |
| 2004/0156804 A1 | 8/2004 | Poterie et al. |
| 2004/0166076 A1 | 8/2004 | Ferrari et al. |
| 2004/0166133 A1 | 8/2004 | Cavazzuti et al. |
| 2004/0176487 A1 | 9/2004 | Svedberg et al. |
| 2004/0186259 A1 | 9/2004 | Brehm et al. |
| 2004/0197286 A1 | 10/2004 | Robert et al. |
| 2004/0223987 A1 | 11/2004 | Ferrari |
| 2004/0228886 A1 | 11/2004 | Ding et al. |
| 2004/0247549 A1 | 12/2004 | Lu et al. |
| 2005/0008667 A1 | 1/2005 | Liechty et al. |
| 2005/0014674 A1 | 1/2005 | Liechty et al. |
| 2005/0043209 A1 | 2/2005 | Schmiedel et al. |
| 2005/0089540 A1 | 4/2005 | Uchiyama et al. |
| 2005/0118126 A1 | 6/2005 | Rollat et al. |
| 2005/0148753 A1 | 7/2005 | Nguyen-Kim et al. |
| 2005/0163741 A1 | 7/2005 | Zech |
| 2005/0169873 A1 | 8/2005 | Rollat et al. |
| 2005/0169874 A1 | 8/2005 | Zofchak et al. |
| 2005/0209428 A1 | 9/2005 | Tamareselvy |
| 2005/0220740 A1 | 10/2005 | Dumousseaux |
| 2005/0220741 A1 | 10/2005 | Dumousseaux |
| 2005/0249691 A1 | 11/2005 | Monks et al. |
| 2005/0257330 A1 | 11/2005 | Noecker et al. |

(56) References Cited

U.S. PATENT DOCUMENTS

| | | |
|---|---|---|
| 2005/0276831 A1 | 12/2005 | Dihora et al. |
| 2005/0287100 A1 | 12/2005 | Lebre |
| 2005/0287103 A1 | 12/2005 | Filippi et al. |
| 2005/0287182 A1 | 12/2005 | Monks et al. |
| 2005/0287183 A1 | 12/2005 | Lebre |
| 2006/0045890 A1 | 3/2006 | Gonzalez et al. |
| 2006/0045893 A1 | 3/2006 | Yu et al. |
| 2006/0051311 A1 | 3/2006 | Walter et al. |
| 2006/0073106 A1 | 4/2006 | Berg-Schultz et al. |
| 2006/0078519 A1 | 4/2006 | Lion et al. |
| 2006/0083762 A1 | 4/2006 | Brun et al. |
| 2006/0099550 A1 | 5/2006 | Faasse et al. |
| 2006/0120983 A1 | 6/2006 | Blin et al. |
| 2006/0134049 A1 | 6/2006 | Keenan et al. |
| 2006/0171984 A1 | 8/2006 | Cromack et al. |
| 2006/0193789 A1 | 8/2006 | Tamarkin et al. |
| 2006/0216250 A1 | 9/2006 | Schultz et al. |
| 2006/0233728 A1 | 10/2006 | Sagawa et al. |
| 2006/0281650 A1 | 12/2006 | Keenan et al. |
| 2006/0287219 A1 | 12/2006 | Dykstra et al. |
| 2007/0032605 A1 | 2/2007 | Harashina |
| 2007/0105977 A1 | 5/2007 | Gabriel et al. |
| 2007/0167565 A1 | 7/2007 | Rische et al. |
| 2007/0183992 A1 | 8/2007 | Dumousseaux et al. |
| 2007/0183997 A9 | 8/2007 | Lebre et al. |
| 2007/0189980 A1 | 8/2007 | Zhang et al. |
| 2007/0197704 A1 | 8/2007 | Walter et al. |
| 2007/0207222 A1 | 9/2007 | Yu et al. |
| 2007/0251026 A1 | 11/2007 | Lalleman et al. |
| 2008/0044373 A1 | 2/2008 | Ilekti et al. |
| 2008/0044445 A1 | 2/2008 | Rubin |
| 2008/0045985 A1 | 2/2008 | Gurtner et al. |
| 2008/0138368 A1 | 6/2008 | Lezer |
| 2008/0175875 A1 | 7/2008 | Sunkara |
| 2008/0254074 A1 | 10/2008 | Dussaud et al. |
| 2009/0049623 A1 | 2/2009 | Brown et al. |
| 2009/0056734 A1 | 3/2009 | Bacon |
| 2009/0061004 A1 | 3/2009 | Birkel et al. |
| 2009/0105195 A1 | 4/2009 | O'Brien |
| 2009/0112141 A1 | 4/2009 | Derr |
| 2009/0175928 A1 | 7/2009 | Maier et al. |
| 2009/0196842 A1 | 8/2009 | Zech et al. |
| 2009/0257960 A1 | 10/2009 | Kim et al. |
| 2009/0263338 A1 | 10/2009 | Rolland et al. |
| 2009/0285866 A1 | 11/2009 | Afriat et al. |
| 2010/0003198 A1 | 1/2010 | Stolmeier et al. |
| 2010/0233146 A1 | 9/2010 | McDaniel |
| 2010/0260687 A1 | 10/2010 | Yu et al. |
| 2010/0261629 A1 | 10/2010 | Smets et al. |
| 2010/0297036 A1 | 11/2010 | Feuillette |
| 2010/0325812 A1 | 12/2010 | Panandiker et al. |
| 2010/0325813 A1 | 12/2010 | Dykstra et al. |
| 2011/0010817 A1 | 1/2011 | Theberge et al. |
| 2011/0027211 A1 | 2/2011 | Viala et al. |
| 2011/0046286 A1 | 2/2011 | Lubnin et al. |
| 2011/0117042 A1 | 5/2011 | Viala et al. |
| 2011/0200927 A1 | 8/2011 | Jung et al. |
| 2011/0229430 A1 | 9/2011 | Hawkins et al. |
| 2011/0230474 A1 | 9/2011 | Grigorian et al. |
| 2011/0256311 A1 | 10/2011 | Mattos, Jr. |
| 2011/0272320 A1 | 11/2011 | Alwattari et al. |
| 2011/0274633 A1 | 11/2011 | Vu et al. |
| 2012/0255574 A1 | 10/2012 | Flohr et al. |
| 2013/0084256 A1 | 4/2013 | Li et al. |
| 2013/0161349 A1 | 6/2013 | Pfeiffenberger |
| 2013/0196849 A1 | 8/2013 | Combs et al. |
| 2013/0239344 A1 | 9/2013 | Stolarz, Jr. et al. |
| 2013/0239874 A1 | 9/2013 | Smith et al. |
| 2013/0261255 A1 | 10/2013 | Deyrail et al. |
| 2014/0010776 A1 | 1/2014 | Viala et al. |
| 2014/0044657 A1 | 2/2014 | Kelly et al. |
| 2014/0066496 A1 | 3/2014 | Gunari et al. |
| 2014/0086864 A1 | 3/2014 | Ishimori et al. |
| 2014/0105846 A1 | 4/2014 | Viala et al. |
| 2014/0142191 A1 | 5/2014 | De La Zerda et al. |
| 2014/0147396 A1 | 5/2014 | Sertchook et al. |
| 2014/0170327 A1 | 6/2014 | Dombrowski et al. |
| 2014/0219927 A1 | 8/2014 | Belluscio et al. |
| 2014/0248270 A1 | 9/2014 | Yu et al. |
| 2014/0248340 A1 | 9/2014 | Schwarzentruber et al. |
| 2014/0350269 A1 | 11/2014 | Eiji Borges Sato |
| 2015/0004117 A1 | 1/2015 | Tan et al. |
| 2015/0007849 A1 | 1/2015 | Cajan et al. |
| 2015/0071978 A1 | 3/2015 | Chang |
| 2015/0118331 A1 | 4/2015 | Boam et al. |
| 2015/0119497 A1 | 4/2015 | Matsui et al. |
| 2015/0190450 A1 | 7/2015 | Chang |
| 2015/0238406 A1 | 8/2015 | Pohlmann et al. |
| 2015/0283041 A1 | 10/2015 | Benn et al. |
| 2015/0342845 A1 | 12/2015 | Hwang et al. |
| 2015/0344622 A1 | 12/2015 | Mukerjee et al. |
| 2016/0001099 A1 | 1/2016 | Castro et al. |
| 2016/0058678 A1 | 3/2016 | Smets et al. |
| 2016/0074311 A1 | 3/2016 | Massey-Brooker et al. |
| 2016/0143836 A1 | 5/2016 | Hayes et al. |
| 2016/0175233 A1 | 6/2016 | Benn |
| 2016/0175238 A1 | 6/2016 | Shin et al. |
| 2016/0184195 A1* | 6/2016 | Tan .......... A61K 8/87 |
| | | 424/70.17 |
| 2016/0220475 A1 | 8/2016 | Scherner et al. |
| 2017/0216188 A1 | 8/2017 | Bermudez Agudelo et al. |
| 2017/0258700 A1 | 9/2017 | Kang et al. |
| 2019/0151221 A1 | 5/2019 | Kang et al. |
| 2019/0359786 A1 | 11/2019 | Trahan et al. |
| 2021/0212920 A1 | 7/2021 | Kang et al. |

FOREIGN PATENT DOCUMENTS

| | | |
|---|---|---|
| CN | 1236783 A | 12/1999 |
| CN | 1370063 A | 9/2002 |
| CN | 1370185 A | 9/2002 |
| CN | 1413102 A | 4/2003 |
| CN | 1476320 A | 2/2004 |
| CN | 1487962 A | 4/2004 |
| CN | 1607934 A | 4/2005 |
| CN | 1650840 A | 8/2005 |
| CN | 1708524 A | 12/2005 |
| CN | 1775826 A | 5/2006 |
| CN | 101124256 A | 2/2008 |
| CN | 101130082 A | 2/2008 |
| CN | 101361701 A | 2/2009 |
| CN | 101484130 A | 7/2009 |
| CN | 101980691 A | 2/2011 |
| CN | 102015803 A | 4/2011 |
| CN | 102575051 A | 7/2012 |
| CN | 102895164 A | 1/2013 |
| CN | 103314025 A | 9/2013 |
| CN | 103705401 A | 4/2014 |
| CN | 104188877 A | 12/2014 |
| CN | 105213260 A | 1/2016 |
| CN | 105561841 A | 5/2016 |
| CN | 105764484 A | 7/2016 |
| CN | 109071750 A | 12/2018 |
| DE | 102015204154 A1 | 9/2016 |
| EP | 727981 A1 | 8/1996 |
| EP | 789550 A1 | 8/1997 |
| EP | 923927 A1 | 6/1999 |
| EP | 1058560 A1 | 12/2000 |
| EP | 1082953 A1 | 3/2001 |
| EP | 1090632 A1 | 4/2001 |
| EP | 1090633 A1 | 4/2001 |
| EP | 1092419 A1 | 4/2001 |
| EP | 1155676 A2 | 11/2001 |
| EP | 1161937 A2 | 12/2001 |
| EP | 1216690 A2 | 6/2002 |
| EP | 1218430 A1 | 7/2002 |
| EP | 1289363 A1 | 3/2003 |
| EP | 1417886 A1 | 5/2004 |
| EP | 1419759 A2 | 5/2004 |
| EP | 1440680 A1 | 7/2004 |
| EP | 1481661 A2 | 12/2004 |
| EP | 1491179 A2 | 12/2004 |
| EP | 1579841 A1 | 9/2005 |
| EP | 1579849 A1 | 9/2005 |

(56) References Cited

FOREIGN PATENT DOCUMENTS

| | | | |
|---|---|---|---|
| EP | 1598046 A1 | 11/2005 |
| EP | 1604634 A1 | 12/2005 |
| EP | 1707182 A1 | 10/2006 |
| EP | 1707183 A1 | 10/2006 |
| EP | 1773906 A1 | 4/2007 |
| EP | 1800671 A1 | 6/2007 |
| EP | 1903065 A2 | 3/2008 |
| EP | 2209472 A1 | 7/2010 |
| EP | 2271304 A1 | 1/2011 |
| EP | 2391424 A2 | 12/2011 |
| EP | 2591772 A1 | 5/2013 |
| EP | 2611466 A2 | 7/2013 |
| EP | 2726067 A1 | 5/2014 |
| EP | 2858630 A1 | 4/2015 |
| EP | 2859794 A1 | 4/2015 |
| EP | 2867298 A1 | 5/2015 |
| EP | 2925296 A1 | 10/2015 |
| EP | 2995217 A1 | 3/2016 |
| EP | 3020454 A1 | 5/2016 |
| FR | 2801209 A1 | 5/2001 |
| FR | 2815350 A1 | 4/2002 |
| FR | 2816834 A1 | 5/2002 |
| FR | 2835529 A1 | 8/2003 |
| FR | 2892931 A1 | 5/2007 |
| FR | 2902655 A1 | 12/2007 |
| FR | 2940093 A1 | 6/2010 |
| FR | 2957347 A1 | 9/2011 |
| FR | 2967062 A1 | 5/2012 |
| JP | H06362 A | 1/1994 |
| JP | H1080973 A | 3/1998 |
| JP | 2002-020451 A | 1/2002 |
| JP | 2003-081742 A | 3/2003 |
| JP | 2004-203917 A | 7/2004 |
| JP | 2004-256694 A | 9/2004 |
| JP | 2006-290845 A | 10/2006 |
| JP | 2009-292854 A | 12/2009 |
| JP | 2010-132568 A | 6/2010 |
| JP | 2010-163389 A | 7/2010 |
| JP | 2011-173851 A | 9/2011 |
| JP | 2011-246352 A | 12/2011 |
| JP | 2012-057110 A | 3/2012 |
| JP | 2013-502494 A | 1/2013 |
| JP | 2016-094362 A | 5/2016 |
| KR | 20080064230 A | 7/2008 |
| KR | 20090058294 A | 6/2009 |
| KR | 20090081582 A | 7/2009 |
| KR | 20110062277 A | 6/2011 |
| KR | 20140078356 A | 6/2014 |
| KR | 20140093349 A | 7/2014 |
| KR | 20140121154 A | 10/2014 |
| WO | WO-1989/007959 A1 | 9/1989 |
| WO | WO-1991/001970 A2 | 2/1991 |
| WO | WO-1994/13354 A1 | 6/1994 |
| WO | WO-1998/13025 A1 | 4/1998 |
| WO | WO-1998/26751 A1 | 6/1998 |
| WO | WO-1998/26756 A1 | 6/1998 |
| WO | WO-1999/12519 A1 | 3/1999 |
| WO | WO-1999/55288 A1 | 11/1999 |
| WO | WO-1999/55290 A1 | 11/1999 |
| WO | WO-1999/55291 A1 | 11/1999 |
| WO | WO-1999/55292 A1 | 11/1999 |
| WO | WO-1999/56708 A1 | 11/1999 |
| WO | WO-2000/14091 A1 | 3/2000 |
| WO | WO-2000/016752 A2 | 3/2000 |
| WO | WO-2000/018367 A1 | 4/2000 |
| WO | WO-2000/027350 A1 | 5/2000 |
| WO | WO-2000/40628 A1 | 7/2000 |
| WO | WO-2001/003652 A2 | 1/2001 |
| WO | WO-2001/024768 A2 | 4/2001 |
| WO | WO-2001/068037 A2 | 9/2001 |
| WO | WO-2001/078691 A1 | 10/2001 |
| WO | WO-2001/087065 A1 | 11/2001 |
| WO | WO-2001/094438 A1 | 12/2001 |
| WO | WO-2002/007699 A1 | 1/2002 |
| WO | WO-2002/039961 A1 | 5/2002 |
| WO | WO-2002/039964 A1 | 5/2002 |
| WO | WO-2002/043490 A1 | 6/2002 |
| WO | WO-2002/043491 A1 | 6/2002 |
| WO | WO-2002/045663 A1 | 6/2002 |
| WO | WO-2002/047620 A2 | 6/2002 |
| WO | WO-2002/047624 A1 | 6/2002 |
| WO | WO-2002/047626 A1 | 6/2002 |
| WO | WO-2002/047628 A1 | 6/2002 |
| WO | WO-2002/047657 A2 | 6/2002 |
| WO | WO-2002/047658 A2 | 6/2002 |
| WO | WO-2002/054997 A1 | 7/2002 |
| WO | WO-2002/055034 A2 | 7/2002 |
| WO | WO-2002/072045 A2 | 9/2002 |
| WO | WO-2003/028678 A1 | 4/2003 |
| WO | WO-2003/094870 A1 | 11/2003 |
| WO | WO-2004/110401 A2 | 12/2004 |
| WO | WO-2005/014777 A2 | 2/2005 |
| WO | WO-2005/017134 A2 | 2/2005 |
| WO | WO-2005/092963 A1 | 10/2005 |
| WO | WO-2006/015718 A1 | 2/2006 |
| WO | WO-2006/062740 A2 | 6/2006 |
| WO | WO-2006/127883 A2 | 11/2006 |
| WO | WO-2006/131403 A1 | 12/2006 |
| WO | WO-2007/057059 A1 | 5/2007 |
| WO | WO-2007/070643 A2 | 6/2007 |
| WO | WO-2007/071886 A2 | 6/2007 |
| WO | WO-2007/077029 A1 | 7/2007 |
| WO | WO-2007/145395 A1 | 12/2007 |
| WO | WO-2008/006677 A1 | 1/2008 |
| WO | WO-2008/006687 A1 | 1/2008 |
| WO | WO-2008/024408 A2 | 2/2008 |
| WO | WO-2008/125406 A2 | 10/2008 |
| WO | WO-2008/133982 A2 | 11/2008 |
| WO | WO-2008/148809 A1 | 12/2008 |
| WO | WO-2009/014347 A2 | 1/2009 |
| WO | WO-2009/053594 A2 | 4/2009 |
| WO | WO-2010/003138 A1 | 1/2010 |
| WO | WO-2010/006442 A1 | 1/2010 |
| WO | WO-2010/037402 A1 | 4/2010 |
| WO | WO-2010/076483 A1 | 7/2010 |
| WO | WO-2010/079468 A2 | 7/2010 |
| WO | WO-2010/086754 A2 | 8/2010 |
| WO | WO-2010/129299 A2 | 11/2010 |
| WO | WO-2011/016140 A1 | 2/2011 |
| WO | WO-2011/016531 A1 | 2/2011 |
| WO | WO-2011/075556 A1 | 6/2011 |
| WO | WO-2011/089709 A1 | 7/2011 |
| WO | WO-2011/126978 A1 | 10/2011 |
| WO | WO-2011/140330 A2 | 11/2011 |
| WO | WO-2012/037445 A2 | 3/2012 |
| WO | WO-2012/063947 A1 | 5/2012 |
| WO | WO-2012/087510 A1 | 6/2012 |
| WO | 2012/105096 A1 | 8/2012 |
| WO | WO-2012/117013 A1 | 9/2012 |
| WO | WO-2012/121704 A1 | 9/2012 |
| WO | WO-2012/168102 A2 | 12/2012 |
| WO | 2013/064596 A1 | 5/2013 |
| WO | WO-2013/068478 A1 | 5/2013 |
| WO | WO-2013/071079 A1 | 5/2013 |
| WO | WO-2013/149323 A1 | 10/2013 |
| WO | 2013/165424 A1 | 11/2013 |
| WO | WO-2014/001574 A1 | 1/2014 |
| WO | WO-2014/001985 A1 | 1/2014 |
| WO | WO-2014/014139 A1 | 1/2014 |
| WO | 2014/111579 A2 | 7/2014 |
| WO | WO-2014/105676 A1 | 7/2014 |
| WO | WO-2014/176515 A2 | 10/2014 |
| WO | WO-2014/210117 A1 | 12/2014 |
| WO | WO-2015/020060 A1 | 2/2015 |
| WO | WO-2015/028417 A1 | 3/2015 |
| WO | WO-2015/028418 A1 | 3/2015 |
| WO | WO-2015/028421 A1 | 3/2015 |
| WO | WO-2015/028424 A1 | 3/2015 |
| WO | WO-2015/051139 A1 | 4/2015 |
| WO | WO-2015/188335 A1 | 12/2015 |
| WO | WO-2016/016315 A1 | 2/2016 |
| WO | WO-2016/058958 A1 | 4/2016 |
| WO | WO-2016/069396 A2 | 5/2016 |
| WO | WO-2016/074683 A1 | 5/2016 |

(56) References Cited

FOREIGN PATENT DOCUMENTS

| WO | WO-2016/087948 A2 | 6/2016 |
|---|---|---|
| WO | WO-2016/096928 A1 | 6/2016 |
| WO | WO-2016/100885 A1 | 6/2016 |
| WO | WO-2016/115257 A2 | 7/2016 |
| WO | WO-2016/138249 A1 | 9/2016 |
| WO | WO-2017/155906 A1 | 9/2017 |

OTHER PUBLICATIONS

U.S. Appl. No. 17/855,239, filed Jun. 30, 2022, Pending.
U.S. Appl. No. 16/128,622, filed Sep. 12, 2018, U.S. Pat. No. 10,842,729, Issued.
U.S. Appl. No. 17/071,198, filed Oct. 15, 2020, Abandoned.
U.S. Appl. No. 16/195,584, filed Nov. 19, 2018, 2019-0151221, Published.
U.S. Appl. No. 17/050,803, filed Oct. 26, 2020, 2021-0212920, Published.
U.S. Appl. No. 15/451,897, filed Mar. 7, 2017, 2017-0258700, Published.
U.S. Appl. No. 17/530,662, filed Nov. 19, 2021, Pending.
Adina, Natpure Hollowbead. Adina Cosmetic Ingredients Ltd., retrieved online at: http://www.cosmeticingredients.co.uk/ingredient/natpure-hollowbead. 2 pages, (2015).
AkzoNobel, Product Specification for Expancel Microspheres, www.expancel.com, 2 pages, (2011).
Araujo et al., Techniques for reducing residual monomer content in polymers: a review. Polymer Engineering and Science. 64 pages, Jul. 1, 2002.
Lochhead et al., Polymers in Cosmetics: Recent Advances. From film-formers to rheology modifiers, polymers serve various functions. Retrieved online at: https://www.happi.com/contents/view_features/2005-11-15/polymers-in-cosmetics-recent-advances. 12 pages, Nov. 15, 2005.
Srivastava et al., Indian Application No. 148/DEL/2010. Bioreactor and Uses Thereof. Filed Jul. 29, 2011. 20 pages.
Teixeira et al., A case study of product engineering: Performance of microencapsulated perfumes on textile applications. AIChE Journal. Jun. 2011;58(6):1939-1950.
Xu et al., Synthesis and Characterization of Cationic Waterborne Polyurethane based Polycarbonate Polyol. China Leather. Nov. 2011;40(21):1-14.
Yao et al., Application of bionic technology in textiles. Textile Dyeing and Finishing Journal. Dec. 2013;35(12):29-33.
Zhang et al., Working Manual of Large Scale Poultry Farm Laboratory. Golden Shield Publishing House. p. 138, Oct. 2013.
Chinese Office Action for Application No. 201880058933.2, dated Aug. 4, 2021, 26 pages.

* cited by examiner

Color Lost from Hair Treated with Cationic WBPU

Color Lost from Hair Treated with Merquat Mixture

Color Lost from Hair Treated with Cationic WBPU

Color Lost from Hair Treated with N-DurHance A-1000

COLOR PROTECTANT COMPOSITIONS

RELATED APPLICATIONS

This application is a continuation of U.S. patent application Ser. No. 17/071,198, filed Oct. 15, 2020, which is a continuation of U.S. patent application Ser. No. 16/128,622, filed Sep. 12, 2018, now U.S. Pat. No. 10,842,729, which claims priority to U.S. Provisional Application No. 62/655,275, filed Apr. 10, 2018 and U.S. Provisional Application No. 62/557,825, filed Sep. 13, 2017, the entire contents of each of which are incorporated herein by reference.

BACKGROUND

Even after long, expensive coloring sessions, consumers who dye their hair report that a significant portion of the hair dye is lost within the first few washes. Most common commercial hair dyes consist of large chromophores (dye molecules) that are deposited within the hair fiber through a process of hair swelling and dye deposition. Since these chromophores are not covalently attached to the hair itself, they commonly leach from the hair during routine washing and conditioning. This is a nuisance for consumers and requires routine trips to the salon and the exhaustive use of chemicals, some of which can cause permanent damage to the hair and harm to the environment. While the search continues for more attractive and environmentally greener ways to dye hair, the need remains for formulations which can reduce the amount of color loss, thereby resulting in fewer trips to the salon and a reduction in the use of harmful chemicals.

SUMMARY

Provided herein are methods of preserving color dye in hair comprising the application of certain cationic polyurethane based compositions. FIGS. 2a and 2b, for example, shows that wash solutions comprising the disclosed cationic polyurethanes result in minimal dye loss when compared to commercially available color protectant resins.

Also provided herein are methods for determining and evaluating the color retention capabilities of cosmetic compositions through the use of dialysis techniques.

DETAILED DESCRIPTION

1. Definitions

Figure 1A:
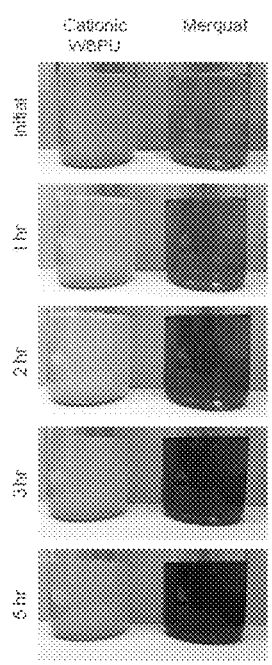
FIG. 1a is a dialysis experiment mimicking hair dye color loss, where reservoir samples containing dye leached from the dialysis tubing show that submersion of dialysis tubing containing hair dye in a 0.8 wt % cationic WBPU solution (left) causes less dye loss from the tubing compared to submersion of the hair dye in a 0.8 wt % solution of Merquat™ 2003 PR (Polyquaternium-53, Lubrizol Advanced Materials) and Merquat™ 100 (Polyquaternium-6, Lubrizol Advanced Materials) (right).

A composition, process, or method described herein that "consists essentially of" a cationic polyurethane and other components means that the recited cationic polyurethane is the only polyurethane present in the recited composition, process, or method. Thus, "consists essentially of" or "consisting essentially of" is open ended for all terms except for the inclusion of additional polyurethanes, i.e., only the recited cationic polyurethane is present.

A composition, process, or method described herein that "consists of" a cationic polyurethane and other components means that only the recited components are present. In other words, "consisting of" excludes any element, step, or ingredient not specified. "Consists of" and "consisting of" are used interchangeably.

"Comprising" is inclusive or open-ended and does not exclude additional, un-recited elements or method steps.

As used herein, "cationic polyurethanes" refer to thermoplastic polymers comprising carbamate (urethane) groups and which bear an overall net positive charge at pH ≤7. In some aspects, the cationic polyurethanes described herein bear an overall net positive charge at pH from about 3.7 to about 6.5, from about 3.7 to about 6.0, or from about 3.7 to about 5.5. Unless otherwise specified, cationic polyurethanes, when used herein, include amphoteric/cationic polyurethanes. In one aspect, however, cationic polyurethanes do not encompass amphoteric/cationic polyurethanes.

As used herein, "amphoteric polyurethanes" refer to thermoplastic polymers comprising carbamate (urethane) groups and which can act both as a cationic or an anionic polyurethanes depending on neutralization method. An "amphoteric/cationic polyurethane" means that the described amphoteric species is one which acts as cationic polyurethane when neutralized with an acid, e.g., lactic acid.

"Young's modulus (or the modulus of elasticity, tensile modulus)" is a measure of the stiffness of a solid polymer film. Young's modulus, E, can be calculated by dividing the tensile stress by the extensional strain in the elastic (initial, linear) portion of the stress—strain curve. The Young's modulus of the cationic polyurethane can be determined by a protocol defined to measure mechanical properties, and is developed in reference to ASTM D638, ASTM D412, test guidelines as described below in Example 2.

The "elongation at break (also known as fracture strain, ultimate elongation)" is the ratio between changed length and initial length after breakage of the solid polymer film. The elongation at break of the cationic polyurethane can be determined by a protocol defined to measure mechanical properties, and is developed in reference to ASTM D638, ASTM D412, test guidelines as described below in Example 2.

The "moisture uptake" is the measure of water adsorbed by the solid polymer film. The method for determining the moisture uptake of the solid polymer film is provided in Example 3.

The "sensory score" is determined by the performance of the hair fixative. In particular, the tress with the composition applied is blow dried for 90 seconds. The tresses are prepared in duplicate and blinded randomly and evaluated for natural feeling and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes.

As used herein, "preserving hair color", "reducing the loss of hair color", "reducing color loss in dyed hair", or similar means i.e. the total color change ($\Delta E$) or total chroma change ($\Delta C$) due to hair dye loss in dyed samples treated with the disclosed composition as measured by colorimetery is less than the total color change ($\Delta E$) or total chroma change ($\Delta C$) in hair which has been dyed but not treated with a disclosed composition.

2. Selection Markers

Provided herein are specific combinations of WBPU properties that have been found to result in cosmetic compositions (e.g., hair products) that are capable of reducing color loss in dyed hair (e.g., human hair). Those properties include e.g., a combination of certain mechanical properties, a combination of certain chemical properties, or a combination of both mechanical and chemical properties.

Young's Modulus, Elongation at Break, and Moisture Uptake

The combination of mechanical properties described herein include the Young's modulus (e.g., above 150 MPa), the elongation at break (e.g., from about 15% to about 300%), and hydrophobicity (moisture uptake, e.g., less than 10%).

In one aspect, the Young's modulus of the cationic polyurethane should be above about 150 MPa. For example, the Young's modulus of the cationic polyurethane in the disclosed compositions may be above about 160 MPa, above about 170 MPa, above about 180 MPa, above about 190 MPa, above about 200 MPa, above about 210 MPa, above about 220 MPa, above about 230 MPa, above about 240 MPa, above about 250 MPa, above about 260 MPa, above about 270 MPa, above about 280 MPa, above about 290 MPa, above about 300 MPa, above about 310 MPa, above about 320 MPa, above about 330 MPa, above about 340 MPa, above about 350 MPa, above about 360 MPa, above about 370 MPa, above about 380 MPa, above about 390 MPa, above about 400 MPa, above about 410 MPa, above about 420 MPa, above about 430 MPa, above about 440 MPa, above about 450 MPa, above about 460 MPa, above about 470 MPa, above about 480 MPa, above about 490 MPa, above about 500 MPa, above about 510 MPa, above about 520 MPa, above about 530 MPa, above about 540 MPa, or above 550 MPa. In other aspects, the Young's modulus of the cationic polyurethane should be between about 150 MPa and about 500 MPa. For example, the Young's modulus of the cationic polyurethane in the disclosed compositions may be between about 150 MPa and about 400 MPa, between about 150 MPa and about 350 MPa, between about 170 MPa and about 390 MPa, between about 180 MPa and about 320 MPa, between about 190 MPa and about 300 MPa, between about 200 MPa and about 290 MPa, or between about 210 MPa and about 280 MPa.

In one aspect, the elongation at break of the cationic polyurethane should be from about 15% to about 300%. For example, the elongation at break of the cationic polyurethane in the disclosed composition may be from about 20% to about 300%, from about 25% to about 300%, from about 40% to about 280%, from about 100% to about 280%, from about 100% to about 250%, from about 150% to about 250%, from about 200% to about 250%, from about 210% to about 250%, about 30 to about 150%, from about 15% to about 150%, from about 150% to about 300%, from about 50% to about 250%; from about 75% to about 225%, or from about 100% to about 200%. The elongation break may be optionally combined with one or more of the Young's modulus values described in the paragraph above or any one of the Young's modulus values described in the remainder of the disclosure.

In one aspect, the moisture uptake of the cationic polyurethane should be less than about 10%. For example, the moisture uptake of the cationic polyurethane in the disclosed compositions may be less than about 9.5%, less than about 9%, less than about 8.5%, less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, less than about 0.5%, or is about 0%. In one aspect, the moisture uptake of the cationic polyurethane in the disclosed compositions should be from about 0% to about 10%. For example, the moisture uptake may be from about 0% to about 8%, from about 2% to about 8%, or from about 3% to about 7%. The moisture uptake may be optionally combined with one or more of the Young's modulus values, one or more of the elongation break values, or both as described in the paragraphs above or in the remainder of the disclosure.

As shown in the Exemplification section below, cationic polyurethanes having the Young's modulus, elongation at break, and moisture uptake described above minimize the color loss in hair which has been dyed e.g., by chemical means.

3. Methods of Use

A method of preserving hair color in color dyed human hair, the method comprising applying to the hair a composition comprising a cationic polyurethane having a Young's modulus above 150 MPa, an elongation at break from about 15% to about 300%, and a moisture uptake of less than 10%. Also provided are methods of preserving hair color in color dyed human hair, the method comprising applying to the hair a composition consisting essentially of a cationic polyurethane; a neutralizer; and an oil, wherein the cationic polyurethane has a Young's modulus above 150 MPa; an elongation at break from about 15% to about 300%; and a moisture uptake of less than 10%.

In some aspects, the cationic polyurethane in the provided methods is a salt of the formula: [W, V, Y and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; X is a neutralizing ion; the molecular weight of W is about 1,000 g/mol; the molar ratio of V:W is 1:0.18 to about 1:0.32; the molar ratio of V:Y is 1:0.24 to about 1:0.72; and the molar ratio of V:Z is 1:0.08 to about 1:0.47. In one alternative, the cationic polyurethane in the provided methods is a salt of the formula: [W, V, Y and Z]X$^-$, wherein W is the product formed from polycarbonate polyol monomer; V is the product formed from polyisocyanate monomer; Y is the product formed from $C_{1-8}$ alkyldiol monomer; Z is the product formed from $C_{1-8}$ aminoalkyldiol monomer; X is a neutralizing ion; the molecular weight of W is about 2,000 g/mol; the molar ratio of V:W is 1:0.08 to about 1:0.18; the molar ratio of V:Y is 1:0.36 to about 1:0.82; and the molar ratio of V:Z is 1:0.08 to about 1:0.49. In another alternative, the cationic polyurethane in the provided methods is a salt of the formula: [W, V, Y and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$ aminoalkyldiol monomer; X is a neutralizing ion; the molecular weight of W is about 3,000 g/mol; the molar ratio of V:W is 1:0.05 to about 1:0.13; the molar ratio of V:Y is 1:0.4 to about 1:0.85; and the molar ratio of V:Z is 1:0.08 to about 1:0.49.

In one alternative the cationic polyurethane in the provided methods is a salt of the formula: [W, V, Y, Z, and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$ aminoalkyldiol monomer; $Z^1$ is the product formed from ethoxylated polyol monomer; X is a neutralizing ion; the molecular weight of W is about 1,000 g/mol; the molar ratio of V:W is 1:0.19 to about 1:0.33; the molar ratio of V:Y is 1:0.19 to about 1:0.7; the molar ratio of V:Z is 1:0.08 to about 1:0.49; and the molar ratio of V:$Z^1$ is 1:0 to about 1:0.03. In another alternative, the cationic polyurethane in the provided compositions is a salt of the formula: [W, V, Y, Z, and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$ aminoalkyldiol monomer; $Z^1$ is the product formed from ethoxylated polyol monomer; X is a neutralizing ion; the molecular weight of W is about 2,000 g/mol; the molar ratio of V:W is 1:0.09 to about 1:0.18; the molar ratio of V:Y is 1:0.31 to about 1:0.8; the molar ratio of V:Z is 1:0.09 to about 1:0.51; and the molar ratio of V:$Z^1$ is 1:0 to about 1:0.03. In another alternative, the cationic polyurethane in the provided methods is a salt of the formula: [W, V, Y, Z, and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$ aminoalkyldiol monomer; $Z^1$ is the product formed from ethoxylated polyol monomer; X is a neutralizing ion; the molecular weight of W is about 3,000 g/mol; the molar ratio of V:W is 1:0.05 to about 1:0.13; the molar ratio of V:Y is 1:0.36 to about 1:0.83; the molar ratio of V:Z is 1:0.09 to about 1:0.52; and the molar ratio of V:$Z^1$ is 1:0 to about 1:0.03.

In another alternative, the cationic polyurethane in the provided methods is a salt of the formula: [W, V, Y, Z, and $Z^2$]X$^-$, wherein W is the product formed from polycarbonate polyol monomer; V is the product formed from polyisocyanate monomer; Y is the product formed from $C_{1-8}$ alkyldiol monomer; Z is the product formed from $C_{1-8}$ aminoalkyldiol monomer; $Z^2$ is the product formed from hydroxylated alkyl acid monomer; X is a neutralizing ion; the molecular weight of W is about 1,000 g/mol the molar ratio of V:W is 1:0.19 to about 1:0.33; the molar ratio of V:Y is 1:0.14 to about 1:0.44; the molar ratio of V:Z is 1:0.08 to about 1:0.47; and the molar ratio of V:$Z^2$ is 1:0.05 to about 1:0.33. In another alternative, the cationic polyurethane in the provided methods is a salt of the formula: [W, V, Y, Z, and Z]X$^-$, wherein W is the product formed from polycarbonate polyol monomer; V is the product formed from polyisocyanate monomer; Y is the product formed from $C_{1-8}$ alkyldiol monomer; Z is the product formed from $C_{1-8}$ aminoalkyldiol monomer; $Z^2$ is the product formed from hydroxylated alkyl acid monomer; X is a neutralizing ion; the molecular weight of W is about 2,000 g/mol; the molar ratio of V:W is 1:0.09 to about 1:0.18; the molar ratio of V:Y is 1:0.26 to about 1:0.53; the molar ratio of V:Z is 1:0.09 to about 1:0.49; and the molar ratio of V:$Z^2$ is 1:0.05 to about 1:0.35. In another alternative, the cationic polyurethane in the provided methods is a salt of the formula: [W, V, Y, Z, and $Z^2$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$ aminoalkyldiol monomer; $Z^2$ is the product formed from hydroxylated alkyl acid monomer; X is a neutralizing ion; and the molecular weight of W is about 3,000 g/mol; the molar ratio of V:W is 1:0.05 to about 1:0.13; the molar ratio of V:Y is 1:0.3 to about 1:0.56; the molar ratio of V:Z is 1:0.09 to about 1:0.5; and the molar ratio of V:$Z^2$ is 1:0.05 to about 1:0.35.

In yet another alternative, V is the product formed from isophorone diisocyanate monomer; Y is the product formed from 1,4-butanediol monomer; and Z is the product formed from 3-(dimethylamino)-1,2-propanediol monomer. In yet another alternative, the cationic polyurethane in the provided methods is a salt of the formula:

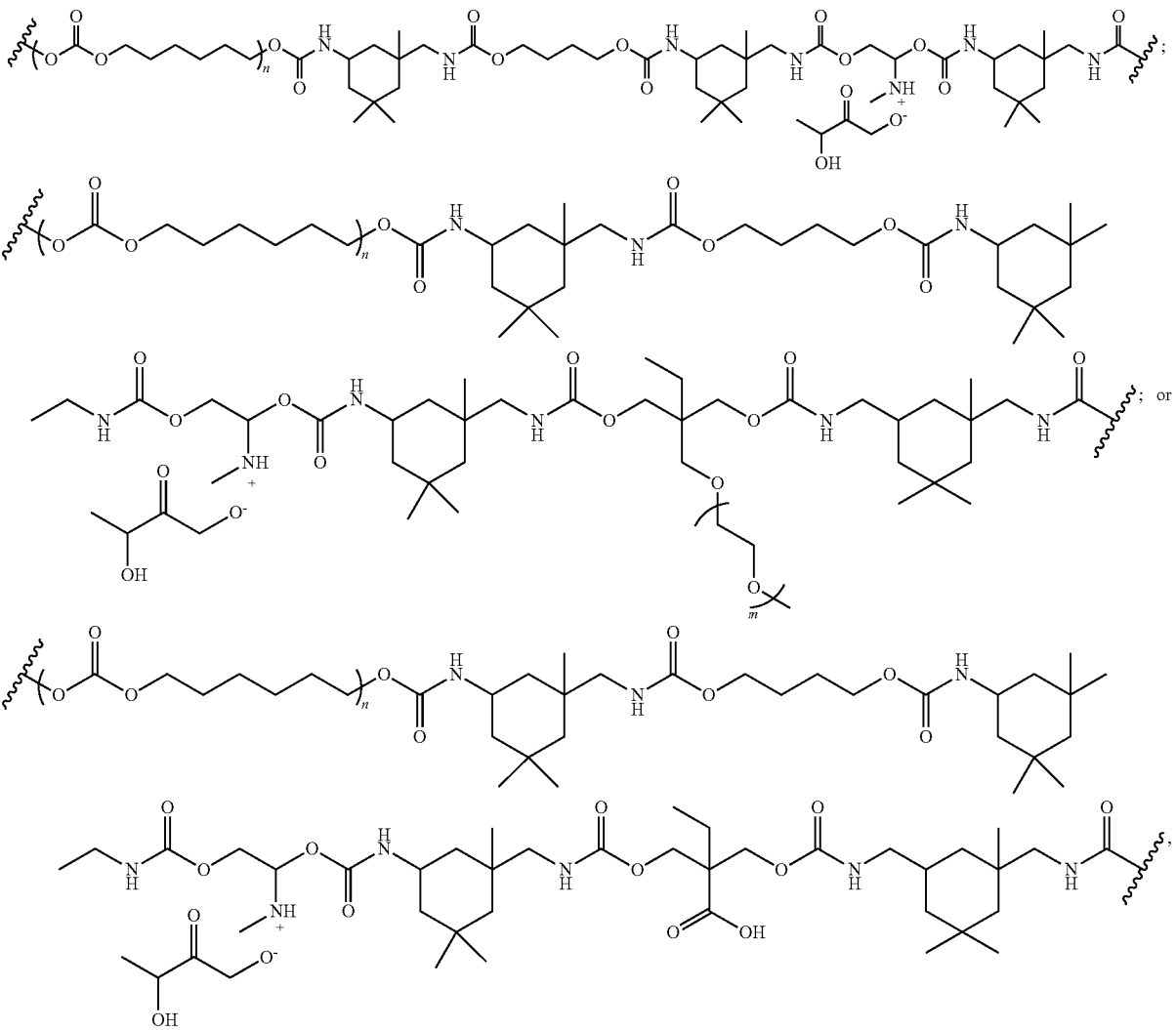

wherein n is 6 to 21 and m is 19 to 31.

In some aspects, the cationic polyurethane in the provided methods is selected from PU-363, PU-399, PU-400, PU-377, PU-404, PU-378, PU-383, PU-398, PU-401, PU-402, PU-403, PU-385, PU-376, PU-408, PU-409, PU-396, PU-413, PU-414, PU-362, and PU-372. In another aspect, the cationic polyurethane in the provided methods is selected from PU-362, PU-376, PU-377, PU-378, and PU-404. In yet another aspect, the cationic polyurethane in the provided methods is selected from PU-363, PU-377, and PU-378.

In some aspects, the cationic polyurethane in the provided methods is dispersed in water.

In some aspects, the cationic polyurethane in the provided methods is in the form of a particle.

In some aspects, the cationic polyurethane in the provided methods comprises uniform particles having an average particle diameter of about 20 to about 80 nm.

In some aspects, the cationic polyurethane in the provided methods comprises bimodal or multimodal particles having an average particle diameter of about 100 to about 300 nm.

In some aspects, the cationic polyurethane in the provided methods is present in an amount of 25% to 35% based on the total weight of the composition.

In some aspects, the compositions described in the provided methods further comprise a neutralizer. The neutralizer may be e.g., an acid neutralizer such as lactic acid. In some aspects, the neutralizer:$C_{1-8}$aminoalkyldiol monomer ratio is from about 0.8 to about 1.2.

In some aspects, the compositions described in the provided methods further comprise an oil. Oils can be selected from mineral, animal, plant or synthetic oils. In one aspect, the oil is linoleic acid or a mixture of fatty acids. Examples include, but are not limited to fragrance oils, emollients, monoterpenoids, fatty alcohols, fatty acids, fatty esters, fatty ethers, fluorinated small molecules (e.g., perfluoromethylcyclopentane, perfluoroperhydrophenanthrene, perfluoro-1,3-dimethylcyclohexane, perfluoromethyldecalin, and perfluoroperhydrobenzyltetralin), and mixtures thereof. In another aspect, the oil is present in an amount ranging from about 0.2 to about 1.65% based on the total weight of the composition. In another aspect, the oil is present in an amount of about 0.2 to about 0.25% based on the total weight of the composition.

In one aspect of the disclosed methods, the composition is applied prior to, during, or after the hair has been dyed. In another aspect, the composition is applied prior to or after the hair has been dyed. In yet another aspect, the composition is applied after the hair has been dyed.

In one aspect of the disclosed methods, the disclosed compositions are applied to the hair with water.

In one aspect of the disclosed methods, the disclosed compositions, when applied to the hair, change the texture and appearance.

In one aspect of the disclosed methods, the disclosed compositions, when applied to the hair, also improve hold, i.e. hair that is formed into a given curl or style retains that curl or style over time.

In one aspect of the disclosed methods, the disclosed compositions, when applied to the hair, also provide sufficient stylability i.e., the composition applied to hair supplies sufficient rigidity and flexibility to form and maintain a style.

In one aspect of the disclosed methods, the disclosed compositions, when applied to the hair, also minimize flyaways i.e., there are minimal individual hair fibers that do not conform to the given curl or style.

In one aspect of the disclosed methods, the disclosed compositions, when applied to the hair, also preserve curl shape i.e., hair that is formed into a given curl retains that curl over time.

In one aspect of the disclosed methods, the disclosed compositions, when applied to the hair, also provide natural curl enhancement i.e., hair that naturally tends to curl displays a more defined and less diffuse curl pattern.

The compositions in the disclosed methods may further comprise an antioxidant. Antioxidants that may be suitable include, but are not limited to, acai oil, alpha lipoic acid, green and white tea, retinol, vitamin C, Vitamin E, butylated hydroxytoluene, butylated hydroxyanisole, coenzyme Q10 (Co Q-10), isoflavones, polyphenols, curcumin, turmeric, pomegranate, rosemary, glutathione, selenium, and zinc.

In an exemplary aspect, an effective amount of a composition described herein may be sprayed or applied onto dry or damp hair before, during, and/or after the hair is dyed As used herein "effective amount" means an amount sufficient to provide color protection.

Also provided herein is a method for determining the color retention properties of a cosmetic composition, the method comprising the step of performing dialysis on a solution comprising the cosmetic composition and at least one color dye; and quantitatively assessing color loss over a period of time. In one aspect, "quantitatively assessing color loss over a period of time" means assessing the total color loss $\Delta E$ or total chroma loss $\Delta C$ according to formula described in Example 4, i.e., $$\Delta E = \sqrt{(L_x - L_0)^2 + (a_x - a_0)^2 + (b_x - b_0)^2} \text{ or}$$

$$\Delta C = \sqrt{(a_x - a_0)^2 + (b_x - b_0)^2}$$

In one aspect, the step of performing dialysis comprises placing a hair dye of interest into dialysis tubing and then placing the dialysis tubing comprising the hair dye in a reservoir bath comprising the composition of interest.

EXEMPLIFICATION

Example 1. Chemical Compositions of Cationic Waterborne Polyurethane

Cationic waterborne polyurethanes were synthesized primarily using polycarbonate diol, 1,4-butanediol (BD), isophorone diisocyanate (IPDI), and 3-(dimethylamino)-1,2-propanediol (DMAPD); selectively, the nonionic chain extenders Tegomer D3403 (ethoxylated polyether-1,3-diol) and 2,2-bis(hydroxymethyl)butyric acid (DMBA) were incorporated in cationic waterborne polyurethanes respectively to achieve desired physical properties. A mild acid, lactic acid, was used as a neutralizer. For each monomer, the molar ratio to NCO is listed in Table 1. Moreover, a beneficial oil could be also incorporated into cationic waterborne polyurethanes to provide improved sensory attributes.

TABLE 1

| PU Name | NCO | Polyol (molar ratio to NCO) | Other diol segment (molar ratio to NCO) | Ionic chain extender (molar ratio to NCO) | Nonionic chain extender (molar ratio to NCO) | Neut. | Degree of Neut. | Oil |
|---|---|---|---|---|---|---|---|---|
| 363 | IPDI | PCD1K_0.29 | BD_0.27 | DMAPD_0.45 | N/A | Lactic acid | 100% | N/A |
| 399 | IPDI | PCD1K_0.29 | BD_0.26 | DMAPD_0.44 | N/A | Lactic acid | 100% | N/A |
| 400 | IPDI | PCD1K_0.20 | BD_0.42 | DMAPD_0.38 | N/A | Lactic acid | 100% | N/A |
| 377 | IPDI | PCD1K_0.28 | BD_0.42 | DMAPD_0.30 | N/A | Lactic acid | 100% | N/A |
| 404 | IPDI | PCD1K_0.29 | BD_0.41 | DMAPD_0.30 | N/A | Lactic acid | 100% | N/A |
| 378 | IPDI | PCD1K_0.28 | BD_0.51 | DMAPD_0.21 | N/A | Lactic acid | 100% | N/A |
| 383 | IPDI | PCD1K_0.28 | BD_0.61 | DMAPD_0.12 | N/A | Lactic acid | 100% | N/A |
| 398 | IPDI | PCD1K_0.29 | BD_0.58 | DMAPD_0.12 | Tegomer_0.0049 | Lactic acid | 100% | N/A |
| 401 | IPDI | PCD1K_0.29 | BD_0.60 | DMAPD_0.12 | N/A | Lactic acid | 100% | N/A |
| 402 | IPDI | PCD3K_0.10 | BD_0.78 | DMAPD_0.12 | N/A | Lactic acid | 100% | N/A |
| 403 | IPDI | PCD1K_0.30 | BD_0.26 | DMAPD_0.44 | N/A | Lactic acid | 80% | N/A |
| 385 | IPDI | PCD1K_0.28 | BD_0.61 | DMAPD_0.12 | N/A | Lactic acid | 110% | N/A |
| 376 | IPDI | PCD1K_0.29 | BD_0.27 | DMAPD_0.45 | N/A | Lactic acid | 100% | Linoleic acid |
| 408 | IPDI | PCD1K_0.28 | BD_0.42 | DMAPD_0.30 | N/A | Lactic acid | 100% | Linoleic acid |
| 409 | IPDI | PCD1K_0.28 | BD_0.42 | DMAPD_0.30 | N/A | Lactic acid | 100% | Mixture of FAs |
| 396 | IPDI | PCD1K_0.28 | BD_0.61 | DMAPD_0.12 | N/A | Lactic acid | 100% | Linoleic acid |
| 413 | IPDI | PCD1K_0.20 | BD_0.56 | DMAPD_0.25 | N/A | Lactic acid | 100% | N/A |
| 414 | IPDI | PCD1K_0.29 | BD_0.56 | DMAPD_0.16 | N/A | Lactic acid | 100% | N/A |
| 362 | IPDI | PCD1K_0.29 | BD_0.27 | DMAPD_0.22 | DMBA_0.22 | Lactic acid | 100% | N/A |
| 372 | IPDI | PCD1K_0.29 | BD_0.27 | DMAPD_0.22 | DMBA_0.22 | Lactic acid | 100% | Linoleic acid |

PCD1K = polycarbonate diol with molecular weight at 1,000 g/mol; PCD3K = polycarbonate diol with molecular weight at 3,000 g/mol.

Overall, inventive cationic waterborne polyurethanes possessed optimal physical properties as defined herein: (1) Young's modulus >150 MPa, (2) Elongation at break between 15% and 300%, and (3) Water uptake (a) below 10% for WBPUs without additive (b) below 8% for WBPUs with additive. See Table 2.

TABLE 2

| PU Name | Young's Modulus (MPa) | Elongation at break (%) | Water Uptake (%) |
|---|---|---|---|
| 363 | 218 ± 21 | 292 ± 21 | 8.01 ± 0.20 |
| 399 | 268 ± 10 | 255 ± 43 | 7.72 ± 0.26 |
| 400 | 326 ± 2 | 24 ± 23 | 7.55 ± 0.40 |
| 377 | 253 ± 10 | 95 ± 10 | 5.23 ± 0.40 |
| 404 | 173 ± 22 | 253 ± 41 | 5.27 ± 0.37 |
| 378 | 228 ± 15 | 163 ± 22 | 3.26 ± 0.33 |
| 383 | 198 ± 12 | 172 ± 48 | 2.46 ± 0.16 |
| 398 | 145 ± 11 | 242 ± 10 | 2.86 ± 0.25 |
| 402 | 170 ± 7 | 47 ± 7 | 1.51 ± 0.17 |
| 376 | 266 ± 12 | 307 ± 25 | 7.51 ± 0.21 |
| 355 | 318 ± 24 | 62 ± 21 | 5.91 ± 0.47 |
| 362 | 295 ± 10 | 170 ± 41 | 2.88 ± 0.93 |
| 372 | 319 ± 42 | 150 ± 45 | 2.87 ± 0.56 |
| 413 | 340 | 10 | 6.22 ± 0.08 |
| 414 | 146 ± 12 | 216 ± 6 | 3.61 ± 0.11 |

Particle size and distribution of cationic waterborne polyurethanes can be divided by two types. Depending on chemical compositions, one type of cationic waterborne polyurethanes showed uniform particle size distribution and average particle diameter was in the range of about 20 to about 80 nm. The other type of cationic waterborne polyurethane showed large particle size and bimodal/multimodal particle size distribution as indicated by average particle sizes in the range of 100 to approximately 300 nm and large standard deviation of particle size. See Table 3.

TABLE 3

| PU Name | Particle Size (TEM, nm) |
|---|---|
| 363 | 29.8 ± 3.9 |
| 399 | 29.9 ± 4.3 |
| 400 | 29.6 ± 5.0 |
| 377 | 34.1 ± 7.5 |
| 378 | 36.6 ± 10.7 |
| 383 | 150.3 ± 112.9 |
| 398 | 111.2 ± 45.4 |
| 402 | 139.6 ± 50.6 |
| 376 | 21.3 ± 4.5 |
| 355 | 41.3 ± 18.3 |
| 362 | 57.0 ± 15.6 |
| 372 | 79.7 ± 29.7 |
| 413 | 60.1 ± 16.7 |
| 414 | 106.2 ± 25.2 |

Example 2. Mechanical Performance

The Young's modulus is a measure of the ability of a material to withstand changes in length when under uniaxial tension or compression. A higher Young's modulus typically indicates that the material is more rigid. The elongation at break, also known as fracture strain, is the ratio between changed length and initial length after breakage of the test specimen. A higher elongation at break expresses the capability of a material to resist fracture.

A comparison of Young's modulus and the elongation at break for the some of the polyurethanes disclosed herein was made to several commercially available polyurethane products. The Young's modulus and the elongation at break can be determined by a protocol defined to measure mechanical properties is developed in compliance with ASTM D638, ASTM D412, test guidelines. In particular, the following protocol can be used to determine the Young's modulus and elongation at break (or ultimate elongation) of dry film of polyurethanes. Testing requires approximately 10-20 min per sample to complete.

Materials:
>25 g polyurethane aqueous dispersion
1 clean rectangular mold (2 mm×20 mm×45 mm) grooved on Teflon sheet per sample
1 clean razor blade
Scotch tape
Universal Testing Machine mounted with extension grip geometry Sample Preparation:
1. Prepare 25 g of 10 wt % WBPU solution from their respective stock solution.
2. Apply 2.5 mL prepared solution in each mold (2 mm×20 mm×45 mm) and allow drying for 2 days to give WBPU film.
3. After it dries out, use a spatula to remove film from the mold.
4. Use the razor blade to cut corners and get film with around 15 mm width and around 150-300 micron thickness. Make sure that the film is free of air bubbles.
5. Label the test film.
6. Cut four pieces of tape (20 mm) per sample and adhere them to both sides of the specimen strip and make a dog-bone shaped sample to improve hold of sample in grip. Store the prepared test films in desiccators for 1-2 hour to fully dry them. Take one sample out of desiccators at a time for testing.

Sample Testing
1. Balance the load registering on the universal testing machine so that it reads 0 Newtons.
2. Use calipers to set a distance of 20 mm between the top and bottom extension grip geometries.
3. Mount a sample in the extension grips and secure tightly, ensuring that the scotch tape is not visible, and that the sample is as close to vertical as possible in both vertical planes.
4. Stretch the sample slightly, by separating the geometries until a force of 2-5 N is registered.
5. Begin a tensile testing run on the universal testing machine at a speed of 100 mm/minute, stopping the test upon sample fracture.
6. Elongation at break is calculated at the elongation at which the material fractures.
7. Young's modulus is calculated as the modulus during the initial, elastic portion of deformation by calculating the slope of a linear fit to that region with an R value >0.99.

a) low modulus and high elongation (Avalure UR 450 (PPG-17/IPDI/DMPA Copolymer), C1004 (Polyurethane-35), Polyderm PE/PA ED (Polyurethane-58), Polyderm PE/PA (Polyurethane-18)), which leads to inferior curl hold (e.g., hold is temporary, transient, or short-lived) or b) high modulus and low elongation (DynamX (Polyurethane-14 and AMP-Acrylates copolymer), DynamX/H$_2$O (Polyurethane-14 and AMP-Acrylates copolymer/water), Luviset PUR (Polyurethane-1)), which leads to a brittle material with low performance (e.g., resin is brittle or fractures) after manipulation.

Example 3. Hydrophobicity/Water Uptake of Polyurethane

The moisture uptake properties, under highly humid environment, of WBPU dry films have been linked to their long lasting hold performance. As such, it is important to be able to reproducibly and accurately evaluate such moisture uptake properties to enable predictive in vitro and in vivo evaluation of WBPU dry films. The following protocol can be used to determine moisture uptake ability of WBPU dry films under high humid environment. Test requires about 2-3 days per sample set to complete Materials
>15 g WBPU solution
1 clean cell culture petri dish (60 mm dia×15 mm H) per sample
Humidity chamber with flexibility to control temperature and relative humidity (RH)

Sample Testing
1. Prepare 15 g of 10 wt % WBPU solution from their respective stock solution.
2. Label cell culture petri dishes for each sample and measure their empty weight ($W_{pd}$).
3. Apply 4 mL prepared solution in each petri dish (3 samples per WBPU and allow to equilibrate for 20 hours at 25° C. and 50% RH in humidity chamber.
4. After equilibration, measure and record sample weight ($W_i$).
5. Place the samples to humidity chamber at 25° C. and 90% RH and allow equilibration to high humidity for 20 hours.
6. Measure and record final sample weight ($W_f$).

Sample Analysis
Calculate % moisture uptake using the following equation:

$$\% \text{ moisture uptake} = \left[ \frac{((Wf - Wpd) - (Wi - Wpd))}{(Wi - Wpd)} \right] \times 100\%$$

Example 4. Dye Preservation

The colorimetry data for hair dye lost in in the presence of the polyurethanes disclosed herein was gathered and compared to hair dye lost in several commercially available color protectant resins. Color loss is determined by evaluating changes in the L*, a*, and b* values for each sample, which are numerical values that can be assigned indicate a sample's color on a white/black scale (L*), a red/green scale (a*), and a blue/yellow scale (b*). The protocol used to determine color loss was gathered using a colorimeter according to the following general procedure. Testing requires approximately 5 min per sample to complete.

Figure 1B:
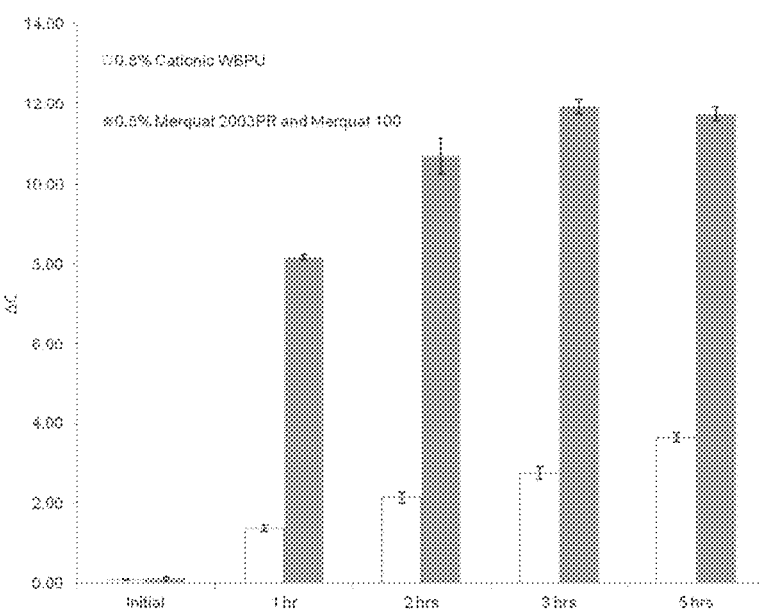
FIG. 1b is the quantification of the color loss using colorimetry, and shows less color loss from dialysis tubing when submerged in a 0.8 wt % cationic WBPU reservoir versus submersion in a reservoir of 0.8 wt % Merquat™ 2003 PR and Merquat™ 100.
Figure 1C:
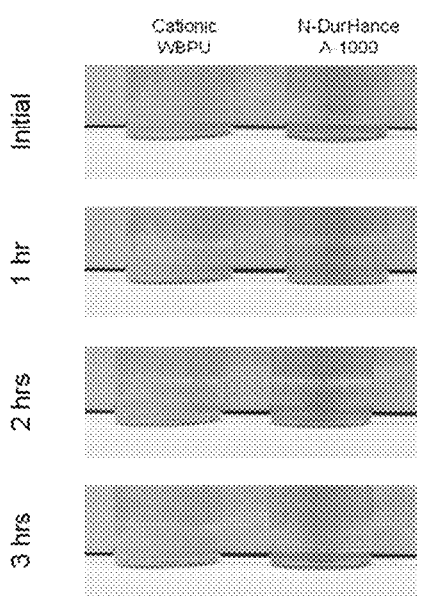
FIG. 1c is a dialysis experiment mimicking hair dye color loss, where reservoir samples containing dye leached from the dialysis tubing show that submersion of dialysis tubing containing hair dye in a 5 wt % cationic WBPU solution causes less dye loss from the tubing compared to submersion of the hair dye in a 5 wt % solution of N-Durhance™ A-1000 (Polyacrylamidopropyltrimonium chloride, Ashland).
Figure 1D:
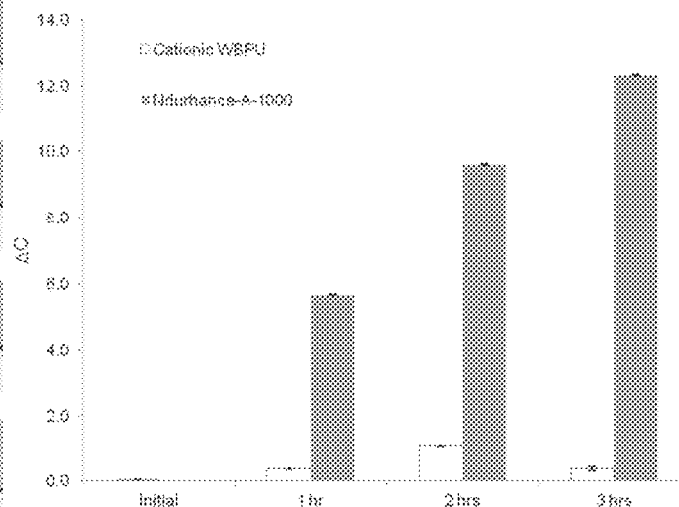
FIG. 1d is the quantification of the color loss using colorimetry, and shows less color loss from dialysis tubing when submerged in a 5 wt % cationic WBPU reservoir versus submersion in a reservoir of 5 wt % solution of N-Durhance™ A-1000.
Figure 1E:
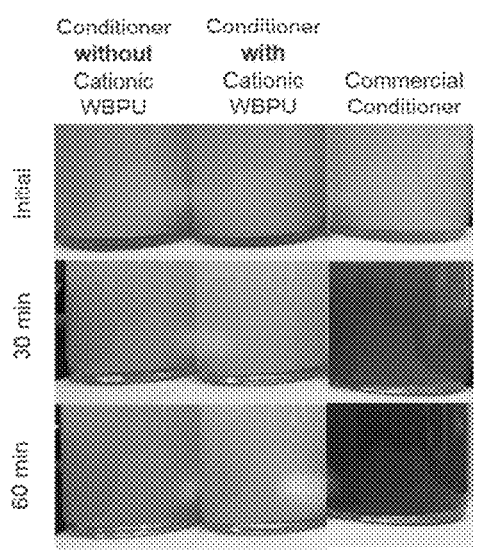
FIG. 1e is a dialysis experiment mimicking hair dye color loss, where conditioner reservoir samples containing dye leached from the dialysis tubing show that submersion of dialysis tubing containing hair dye in a conditioner containing 0.3 wt % cationic WBPU causes less dye loss from the tubing compared to submersion of the hair dye in a commercial conditioner.
Figure 1F:
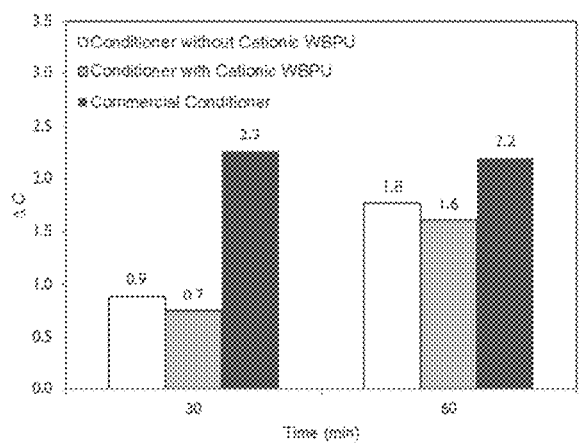
FIG. 1f is the quantification of the color loss using colorimetry (total chroma change (4C), and shows less color loss from dialysis tubing when submerged in a conditioner containing 0.3 wt % cationic WBPU reservoir versus submersion in a reservoir containing blank conditioner or commercial conditioner.
Figure 1G:
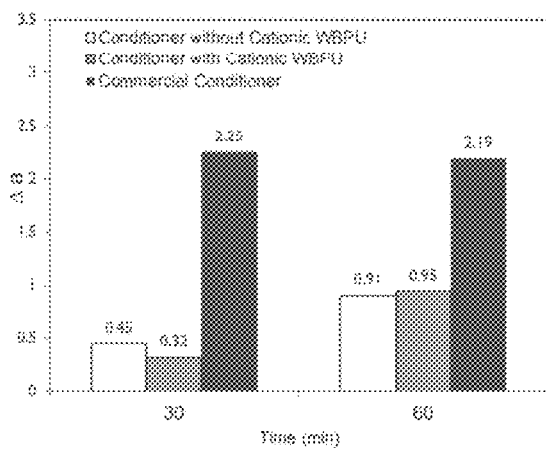
FIG. 1g is the quantification of the color loss using colorimetry (total change in red color ($\Delta a$), and shows less color loss from dialysis tubing when submerged in a conditioner containing 0.3 wt % cationic WBPU reservoir versus submersion in a reservoir containing blank conditioner or commercial conditioner.

1. Perform a calibration of the colorimeter to a pure white calibration standard.
2. To analyze a solution, place a scintillation vial containing the solution on the colorimeter sample stage, and record the L*, a* and b* values.
3. Repeat for all samples of interest.
4. The total color loss ΔE is calculated according to the following formula:

$$\Delta E = \sqrt{(L_x - L_0)^2 + (a_x - a_0)^2 + (b_x - b_0)^2}$$

Where $L_x$ is the L* value of interest and $L_0$ is the initial L* value
Where $a_x$ is the a* value of interest and $a_0$ is the initial a* value
Where $b_x$ is the b* value of interest and $b_0$ is the initial b* value 5. The total chroma loss ΔC is calculated according to the following formula:

$$\Delta C = \sqrt{((a_x - a_0)^2 + (b_x - b_0)^2}$$

Where $a_x$ is the a* value of interest and $a_0$ is the initial a* value
Where $b_x$ is the b* value of interest and $b_0$ is the initial b* value The disclosed cationic polyurethanes were found to minimize dye loss in various polymer systems and therefore contain properties sufficient to delay or prevent dye loss from color treated hair. Here, a novel method for the evaluation of color retention, dialysis, was used to model the in vitro and in vivo color protection results obtained for the cationic WBPU. In each dialysis experiment, hair dye of interest (15 g) was suspended in dialysis tubing with a pore size of 0.5-1 kDa to mimic the pore size of biological materials such as hair keratin. The dialysis tubing was then submerged in a large reservoir bath (300 g) containing a resin of interest, such as the cationic WBPU or commercial color protectant resins. In one experiment, dialysis tubing samples was prepared containing red hair dye and then submerged in either 0.8 wt % cationic WBPU or 0.8 wt % Merquat™ 2003 PR and Merquat™ 100. Samples of the reservoir taken at different timepoints show visually that less hair dye is lost from the dialysis tubing in the presence of the cationic WBPU, compared to the Merquat mixture (FIG. 1a). Results were confirmed by a quantitative colorimetry assessment of the dye lost to the reservoir (FIG. 1b). In another experiment, dialysis tubing samples was prepared containing red hair dye and then submerged in either 5 wt % cationic WBPU or 5 wt % N-DurHance™ A-1000. Samples of the reservoir taken at different timepoints show visually that less hair dye is lost from the dialysis tubing in the presence of the cationic WBPU, compared to N-DurHance™ A-1000 (FIG. 1c). Results were confirmed by a quantitative colorimetry assessment of the dye lost to the reservoir (FIG. 1d).

Figure 2A:
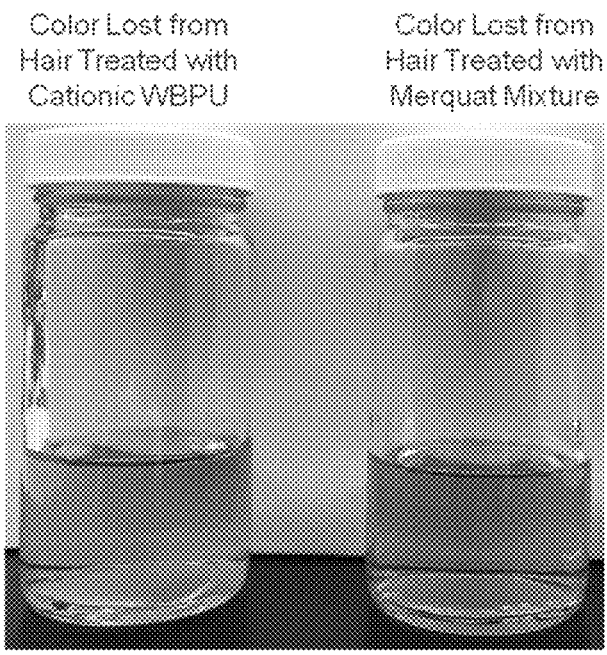
FIG. 2a illustrates the color loss from hair tresses treated with the disclosed cationic polyurethane (left) and dipped in water twenty times, and the color loss from the commercially available color protectant polymers Merquat™ 2003 PR and Merquat™ 100 (right). There is significantly less color loss when hair is treated with the cationic WBPU prior to dipping in water, rather than treatment with the Merquat™ mixture.
Figure 2B:
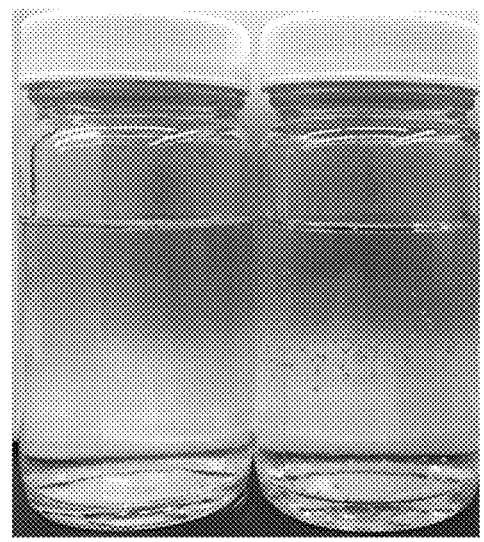
FIG. 2b illustrates the color loss from hair treated with the disclosed cationic polyurethane (left) and dipped in a mild sodium laureth sulfate (surfactant) solution fifteen times, and the color loss from the commercially available color protectant polymer N-Durhance™ A-1000 (right) when dipped in a mild sodium laureth sulfate (surfactant) solution fifteen times. There is significantly less color loss when hair is treated with the cationic WBPU prior to dipping in the surfactant solution.

During a controlled in vitro study mimicking typical dye washing, tresses dyed with red hair dye were treated with solutions containing either a cationic polyurethane or N-DurHance™ A-1000. 1.5 g tresses that were previously dyed with a red hair dye were coated with 0.5 g of 5% cationic WBPU or N-DurHance™ A-1000 solutions and left to sit for 30 seconds, and then dipped 10 times in a jar of 50 mL DI water. The cationic WBPU treatment resulted in far less dye loss (left), compared to the common color protecting polymer N-DurHance™ A-1000 (right). See FIGS. 2a and 2b. The results clearly show that wash solutions containing cationic WBPU result in minimal dye loss, compared to N-DurHance™ A-1000 tress solution.

Figure 3:
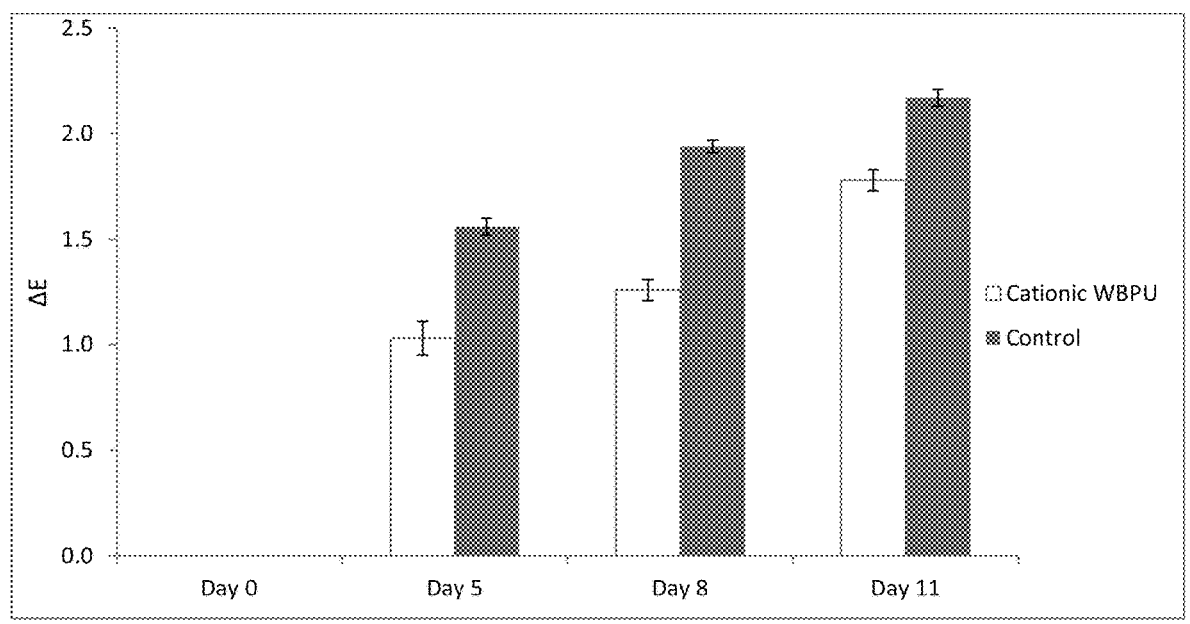
FIG. 3 illustrates the color loss data from an in vivo study in which a consumer with freshly dyed hair was subjected to extended washing and conditioning with formulations containing the disclosed cationic polyurethane on one side of their head and subjected to extended washing and conditioning with formulations without the disclosed cationic polyurethane on the other side of the head. The colorimetry data shows that the color loss over 11 days of washing, as indicated by $\Delta E$, is reduced when using the treatments containing the cationic WBPU. A blinded, trained sensory evaluator determined that there were no detrimental visual or sensory effects observed when using treatments containing the cationic WBPU.

FIG. 3 illustrates the color loss data from an in vivo study in which a consumer with freshly dyed hair was subjected to extended washing and conditioning with formulations containing the disclosed cationic polyurethane on one side of their head and subjected to extended washing and conditioning with formulations without the disclosed cationic polyurethane on the other side of their head. The colorimetry data shows that the color loss over 11 days of washing, as indicated by ΔE, is reduced when using the treatments containing the cationic WBPU. A blinded, trained sensory evaluator determined that there were no detrimental visual or sensory effects observed when using treatments containing the cationic WBPU.

The contents of all references (including literature references, issued patents, published patent applications, and patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A composition comprising a cationic polyurethane, wherein the cationic polyurethane is formed from W, V, Y, Z, and X,
   wherein
   W is a polycarbonate diol with molecular weight of 1,000 g/mol (PCD1K) or a polycarbonate diol with molecular weight of 3,000 g/mol (PCD3K);
   V is isophorone diisocyanate (IPDI);
   Y is 1,4-butanediol (BD);
   Z is 3-(dimethylamino)-1,2-propanediol (DMAPD);
   X is lactic acid;
   the molar ratio of V to W is 1:0.30, 1:0.29, 1:0.28, 1:0.20, or 1:0.10;
   the molar ratio of V to Y is 1:0.78, 1:0.61, 1:0.60, 1:0.58, 1:0.56, 1:0.51, 1:0.42, 1:0.41, 1:0.27, or 1:0.26; and
   the molar ratio of V to Z is 1:0.45, 1:0.44, 1:0.38, 1:0.30, 1:0.25, 1:0.22, 1:0.21, 1:0.16, or 1:0.12.

2. The composition of claim 1, wherein
   W is PCD1K;
   the molar ratio of V to W is 1:0.30, 1:0.29, 1:0.28, or 1:0.20;
   the molar ratio of V to Y is 1:0.61, 1:0.60, 1:0.58, 1:0.56, 1:0.51, 1:0.42, 1:0.41, 1:0.27, or 1:0.26; and
   the molar ratio of V to Z is 1:0.45, 1:0.44, 1:0.38, 1:0.30, 1:0.25, 1:0.22, 1:0.21, 1:0.16, or 1:0.12.

3. The composition of claim 1, wherein
   W is PCD3K;
   the molar ratio of V to W is 1:0.10;
   the molar ratio of V to Y is 1:0.78; and
   the molar ratio of V to Z is 1:0.12.

4. The composition of claim 1, wherein the cationic polyurethane further comprises ethoxylated polyether-1,3-diol (Tegomer), wherein the molar ratio of V to Tegomer is 1:0.0049.

5. The composition of claim 4, wherein the molar ratio of V to W is 1:0.29; the molar ratio of V to Y is 1:0.58; and the molar ratio of V to Z is 1:0.12.

6. The composition of claim 1, wherein the cationic polyurethane further comprises 2,2-bis(hydroxymethyl)butyric acid (DMBA), wherein the molar ratio of V to DMBA is 1:0.22.

7. The composition of claim 6, wherein the molar ratio of V to W is 1:0.29; the molar ratio of V to Y is 1:0.27; and the molar ratio of V to Z is 1:0.22.

8. The composition of claim 7, wherein the cationic polyurethane further comprises linoleic acid.

9. The composition of claim 1, wherein the cationic polyurethane further comprises a mixture of fatty acids.

10. The composition of claim 9, wherein the molar ratio of V to W is 1:0.28; the molar ratio of V to Y is 1:0.42; and the molar ratio of V to Z is 1:0.30.

11. The composition of claim 1, wherein the cationic polyurethane further comprises linoleic acid.

12. The composition of claim 11, wherein the molar ratio of V to W is 1:0.29 or 1:0.28; the molar ratio of V to Y is 1:0.61, 1:0.42, or 1:0.27; and the molar ratio of V to Z is 1:0.45, 1:0.30, or 1:0.12.

13. The composition of claim 1, wherein the cationic polyurethane is dispersed in water.

14. The composition of claim 1, wherein the cationic polyurethane is in the form of a particle.

15. The composition of claim 1, wherein the cationic polyurethane comprises uniform particles having an average particle diameter of 20 to 80 nm.

16. The composition of claim 1, wherein the cationic polyurethane comprises bimodal or multimodal particles having an average particle diameter of 100 to 300 nm.

17. The composition of claim 1, wherein the cationic polyurethane is present in an amount of 25% to 35% based on the total weight of the composition.

* * * * *